United States Patent [19]
Hawkins et al.

[11] Patent Number: 5,638,997
[45] Date of Patent: Jun. 17, 1997

[54] BONE CEMENT INJECTOR GUN

[75] Inventors: Michael E. Hawkins, Columbus City; Stephen H. Hoag; Kirt L. Case, both of Warsaw, all of Ind.; Kwan-Ho Chan, Lubbock, Tex.

[73] Assignee: Zimmer, Inc., Warsaw, Ind.

[21] Appl. No.: 529,814

[22] Filed: Sep. 18, 1995

[51] Int. Cl.⁶ .................................................. A67D 5/42
[52] U.S. Cl. .......................... 222/391; 222/327; 604/209; 606/94; 74/141.5; 74/169; 74/516; 74/522
[58] Field of Search .......................... 222/327, 391; 606/92, 93, 94, 95; 604/71, 181, 187, 207, 209, 282; 74/141.5, 169, 516, 522

[56] References Cited

U.S. PATENT DOCUMENTS

| 2,305,238 | 12/1942 | Coates | 71/169 |
|---|---|---|---|
| 2,732,102 | 1/1956 | Ekins | 222/327 |
| 2,750,943 | 6/1956 | Dann | 128/235 |
| 3,029,653 | 4/1962 | Nilsson | 222/391 X |
| 3,053,457 | 9/1962 | Trumbull et al. | 239/142 |
| 3,141,583 | 7/1964 | Mapel et al. | 222/309 |
| 3,160,156 | 12/1964 | Tyler | 128/236 |
| 3,193,146 | 7/1965 | Isgriggs et al. | 222/82 |
| 3,255,747 | 6/1966 | Cochran et al. | 128/92 |
| 3,894,663 | 7/1975 | Carhart et al. | 222/309 |
| 4,090,639 | 5/1978 | Campbell et al. | 222/43 |
| 4,338,925 | 7/1982 | Miller | 128/92 E |
| 4,339,058 | 7/1982 | Wendt | 222/309 |
| 4,342,310 | 8/1982 | Lindmayer et al. | 129/207.25 |
| 4,356,938 | 11/1982 | Kayser | 222/327 |
| 4,364,388 | 12/1982 | Cech | 128/234 |
| 4,406,654 | 9/1983 | Bristow | 604/209 |
| 4,425,121 | 1/1984 | Young et al. | 604/209 |
| 4,429,589 | 2/1984 | Stocker | 74/516 X |
| 4,546,767 | 10/1985 | Smith | 128/92 E |
| 4,569,662 | 2/1986 | Dragan | 433/89 |
| 4,619,613 | 10/1986 | Dragan | 433/90 |
| 4,671,263 | 6/1987 | Draenert | 128/92 VO |
| 4,738,664 | 4/1988 | Prindle | 604/228 |
| 4,768,955 | 9/1988 | Hirdes | 433/89 |
| 4,787,893 | 11/1988 | Villette | 604/188 |
| 4,840,294 | 6/1989 | Ernst | 222/391 X |
| 4,861,339 | 8/1989 | Jonischkeit | 605/187 X |
| 4,966,601 | 10/1990 | Draenert | 606/92 |
| 4,973,334 | 11/1990 | Ziemann | 606/92 |
| 4,994,065 | 2/1991 | Gibbs et al. | 606/92 |
| 5,022,563 | 6/1991 | Marchitto et al. | 222/391 X |
| 5,125,836 | 6/1992 | Dragan et al. | 433/90 |
| 5,197,635 | 3/1993 | Chang | 222/137 |
| 5,304,147 | 4/1994 | Johnson et al. | 604/183 |
| 5,381,931 | 1/1995 | Chang | 222/309 |
| 5,431,654 | 7/1995 | Nic | 606/92 |

FOREIGN PATENT DOCUMENTS

WO89/01322  2/1989  WIPO ........................... A61F 2/46

Primary Examiner—Andres Kashnikow
Assistant Examiner—Kenneth Bomberg
Attorney, Agent, or Firm—Cary R. Reeves

[57] ABSTRACT

A paste injector gun, especially adapted for injecting bone cement, has first and second mechanical advantages corresponding to different portions of the trigger stroke. The first mechanical advantage is greater than the second such that the first facilitates pressurizing the bone cement and the second facilitates high volume dispensing of the bone cement. The injector gun also includes a pair of U-shaped slots. One of the slots is sized to accept a large cement cartridge and the other slot is sized to accept a small cement cartridge.

17 Claims, 4 Drawing Sheets

FIG. I

BONE CEMENT INJECTOR GUN

BACKGROUND OF THE INVENTION

The present invention relates to injector guns for dispensing pastes, and more particularly, to injector guns that can dispense paste from a cartridge both at low pressure and high volume for filling a void and at high pressure and low volume for pressurizing the paste in the void. The present invention further includes means for connecting the injector gun to cartridges having different diameters.

Prior art injector guns have a trigger mechanism that includes a trigger in the form of a lever. The trigger includes an input end, an output end and a fulcrum between the ends. When the input end is squeezed by the user, the trigger pivots about the fulcrum causing the output end to move. The mechanical advantage of an injector gun is the amount the force applied to the input end is multiplied at the output end and can be calculated as the ratio of the length of the trigger from the fulcrum to the input end over the length of the trigger from the fulcrum to the output end. A high mechanical advantage multiplies the force more but generates less motion at the output end than does a low mechanical advantage. Therefore, a high mechanical advantage facilitates generating a high pressure in the paste but extrudes a low volume of paste whereas a low mechanical advantage generates a low pressure in the paste but extrudes a high volume of paste.

A typical application for paste injector guns is for dispensing bone cement from a cartridge into the intramedullary canal of the femur. Miller discloses such an injector gun in U.S. Pat. No. 4,338,925. Miller teaches the advantage of improved implant fixation that results from pressurizing the cement after filling the canal in order to force the cement into bony interstices. Therefore, Miller requires an injector gun with a relatively high mechanical advantage. However, as is typical of most injector guns, Miller's injector gun utilizes a trigger mechanism with a constant mechanical advantage that is a compromise between a low mechanical advantage that delivers a high flow rate for rapid filling and a high mechanical advantage that delivers high pressure for pressurizing the cement. To increase the flow of cement, the surgeon must squeeze the trigger faster. To increase the pressure on the cement, the surgeon must squeeze the trigger harder.

Some investigators have provided injector guns with user adjustable mechanical advantages. In U.S. Pat. No. 5,197,635, Chang teaches a mechanism that includes a bearing element that is adjustable up and down on the trigger and held in place by a set screw. By moving the bearing element, the output length of the trigger is changed and thus the mechanical advantage is changed. In U.S. Pat. No. 5,381,931, Chang teaches a different mechanism for selectively lengthening the output length of the trigger comprising an eccentric rotatable element attached to the output end of the trigger. Finally, in U.S. Pat. No. 5,431,654, Nic teaches a mechanism comprising two pawls attached to the trigger. The pawls are of a length and orientation such that one provides a high mechanical advantage and the other provides a low mechanical advantage. The desired pawl is engaged by means of a switch activated by the surgeon.

A disadvantage of prior art injector guns with user adjustable mechanical advantages is the need for additional parts and the resulting complexity in the trigger mechanism. Another disadvantage is the need to adjust a screw or move a switch in order to change the mechanical advantage. This adjustment typically requires both of the user's hands to effect the change. A further disadvantage of prior art cement injector guns is that they are configured to connect only to a cement cartridge having a single specified diameter. These prior art cement injector guns are therefore incapable of dispensing cement from differently sized cartridges such as from different manufacturers or different styles or sizes from the same manufacturer.

SUMMARY OF THE INVENTION

The present invention solves these problems of the prior art by providing a paste injector gun, especially adapted for injecting bone cement, having first and second mechanical advantages corresponding to different portions of the trigger stroke. The first mechanical advantage is greater than the second such that the first facilitates pressurizing the bone cement and the second facilitates high volume dispensing of the bone cement.

The two mechanical advantages are accomplished by providing a trigger mechanism with a trigger lever pivotably connected to a drive plate at the output end. The trigger mechanism includes two fulcrums which provide two sequential centers of rotation. In the initial position, the first fulcrum is engaged. As the trigger is squeezed, a high mechanical advantage enables cement pressurization because the first fulcrum is close to the output end of the trigger lever. At the end of this first stage of trigger travel, the second fulcrum is engaged. During the second stage of trigger travel, the trigger lever pivots about the second fulcrum. This results in a higher flow volume because the second pivot point is further from the output end of the trigger lever. With the present invention there are no screws or switches which must be adjusted to change mechanical advantage. The two mechanical advantages are designed into each squeeze of the trigger. The first portion of the trigger stroke produces high pressure and the second portion of the trigger stroke produces high flow volume. If high flow is desired, full strokes are used. If high pressure is desired, short strokes are used. The injector gun of the present invention also includes a pair of U-shaped slots for gripping a bone cement containing cartridge. One of the slots is sized to accept a large cement cartridge. The other slot is sized to accept a small cement cartridge.

DETAILED DESCRIPTION OF THE INVENTION

Figure 1:
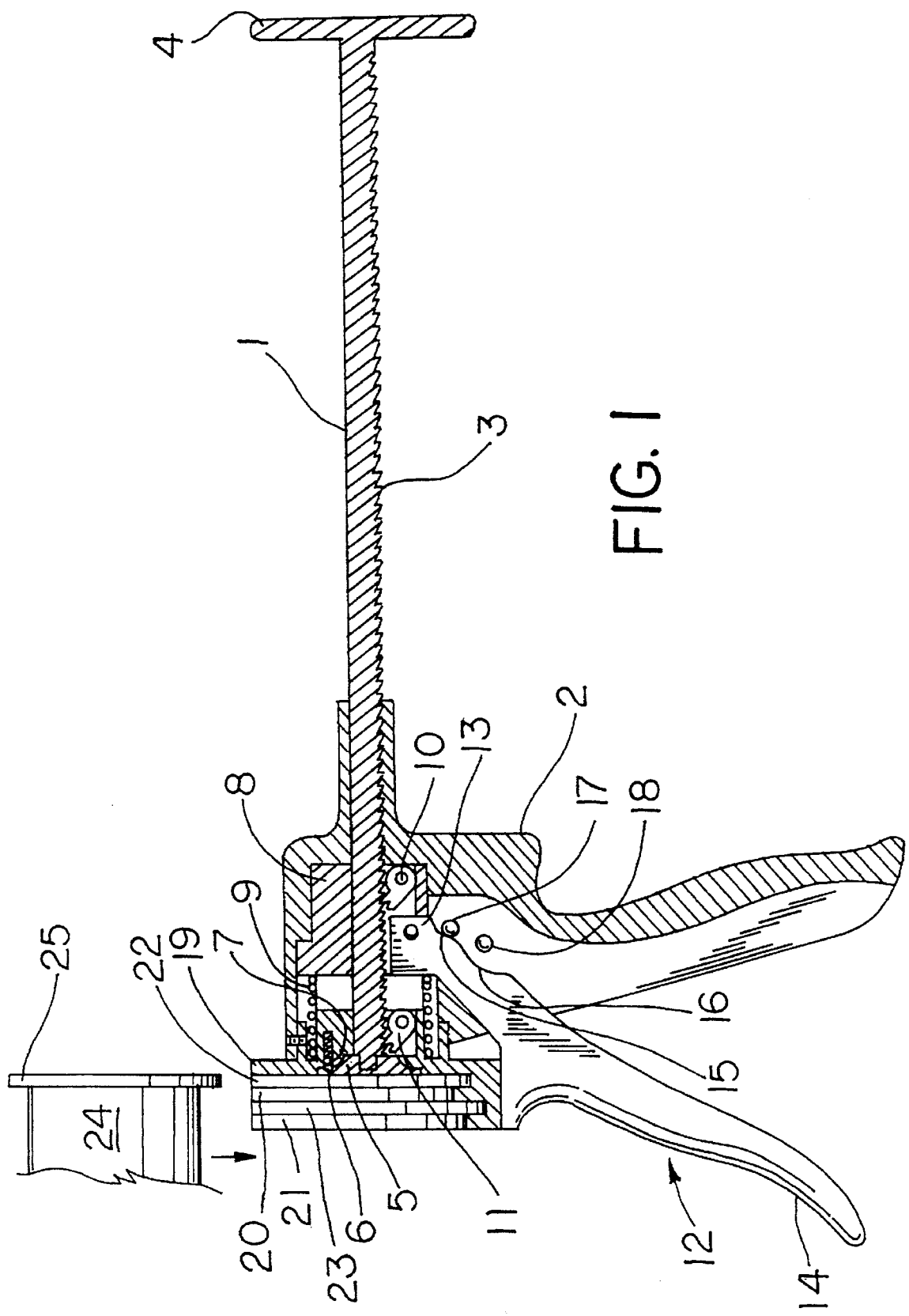
FIG. 1 is a side cross-sectional view of the cement injector gun of the present invention.
Figure 2:
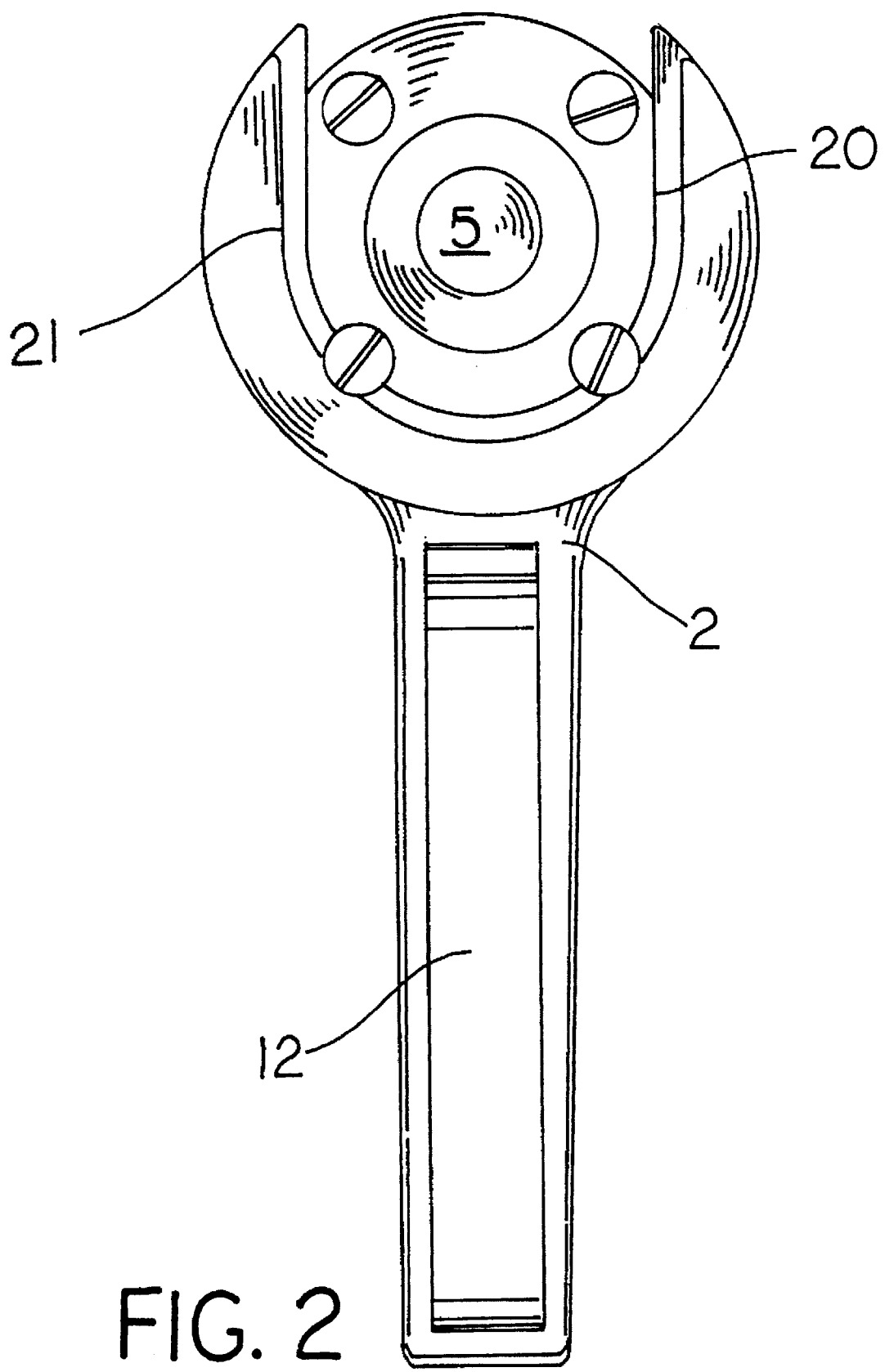
FIG. 2 is an end view of the cement injector gun of FIG. 1.

FIGS. 1 and 2 depict a cement injector gun according to the present invention. A shaft 1 is mounted for axial translation within a housing 2. The shaft includes teeth 3 formed on a portion of its circumference and along its length. A handle 4 is attached to one end of the shaft 1 and a shaft plate 5 is attached to the other end of the shaft 1. The shaft plate 5 contains a recess 6 in its back side. A spring loaded plunger 7 is mounted in the housing behind the shaft plate 5 such that when the teeth 3 are oriented downwardly, the plunger 7 is aligned with the recess 6. A drive plate 8 is mounted for axial translation within the housing 2 and is coaxial with and surrounds the shaft 1. A return spring 9 biases the drive plate 8 rearwardly in the housing. The drive plate 8 carries a drive ratchet 10 rotatably mounted on the drive plate 8. A spring biases the drive ratchet 10 into contact with the shaft 1 such that the drive ratchet 10 will engage the teeth 3 when they are oriented downwardly. A retaining ratchet 11 is rotatably mounted on the housing 2 and it is also spring biased into contact with the shaft 1 such that the retaining ratchet 11 will engage the teeth 3 when they are oriented downwardly. The injector gun includes a trigger having a trigger lever 12 pivotally attached to the drive plate 8 at the trigger lever's output end 13. The input end 14 of the trigger lever 12 extends from the housing 2. The trigger lever 12 also includes first and second bearing portions 15 and 16. First and second fulcrums, 17 and 18, are attached to the housing 2 in alignment with the first and second bearing portions 15 and 16. In the embodiment shown in FIG. 1, the fulcrums are in the form of cylindrical pins attached to the housing and the being portions are in the form of scalloped regions formed on the trigger. A cartridge adapter 19 is mounted on the front of the housing 2. The cartridge adapter 19 contains first and second U-shaped slots, 20 and 21, lying on a common axis in axial alignment with the shaft 1. The U-shaped slots lie in parallel planes to one another. The second U-shaped slot 21 has a larger radius than the first U-shaped slot 20. The U-shaped slots are shaped to engage a cartridge 24 having a rim 25. Each U-shaped slot includes a peripheral groove 22 and 23 to engage the rim 25 to prevent the cartridge from moving forward as the shaft presses against the cartridge. The first U-shaped slot is at least 10% narrower, preferably at least 20% narrower than the second slot. Therefore, first U-shaped slot 20 is sized for a small cartridge and the second U-shaped slot 21 is sized for a large cartridge. The first U-shaped slot 20 is positioned on the common axis nearer to the trigger mechanism than the second U-shaped slot 21 such that a cartridge 24 engaged with the first U-shaped slot 20 will extend through the second U-shaped slot 21 and a cartridge engaged with the second U-shaped slot 21 will not extend through the first U-shaped slot 20.

Referring now to FIGS. 1–5, the function of the cement injector gun will be explained. In use the handle 4 is turned until the teeth 3 disengage the ratchets 10 and 11. The shaft 1 is then pulled backward until the plunger 7 is depressed and the shaft plate 5 is fully seated in the housing 2. The handle 4 is then rotated until the teeth 3 are in alignment with the ratchets 10 and 11. As the teeth 3 come into alignment with the ratchets 10 and 11, the recess 6 will come into alignment with the plunger 7 and the plunger 7 will pop out to extend into the recess 6. The popping of the plunger 7 into the recess 6 is thus an audible and tactile indicator of proper tooth-to-ratchet alignment. With the shaft 1 fully retracted, a cartridge 24 is slid into the appropriate slot, 20 or 21, of the cartridge adapter 19.

To dispense cement, the trigger is squeezed by applying pressure to the input end 14 of the trigger lever 12. The trigger has a range of rotation from the rest position shown in FIG. 3 to the stop position shown in FIG. 5. In the preferred embodiment, the range of rotation is divided into two stages. The first stage is from the initial rest position to an intermediate position where the center of rotation changes from the first fulcrum to the second fulcrum. The second stage is from this intermediate position to the stop position. During the first stage, the first bearing portion 15 contacts the first fulcrum 17 providing a first center of rotation. The trigger lever 12 pivots about the first fulcrum 17 causing the drive plate 8 and drive ratchet 10 to move forward. The drive ratchet 10 presses against the teeth 3 thus driving the shaft 1 forward as well. As the shaft moves forward, the retaining ratchet 11 pivots against its biasing spring and allows the teeth 3 to slip by it. The forward moving shaft plate 5 engages the cartridge 24 and forces cement from it.

Figure 4:
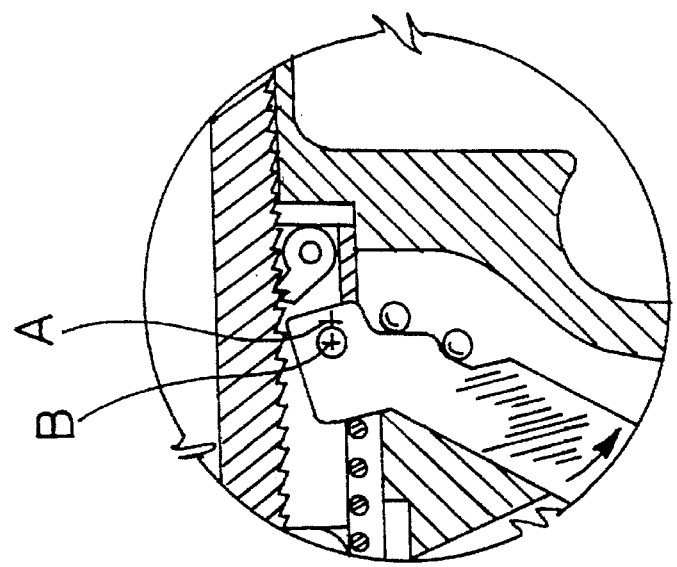
Figure 3:
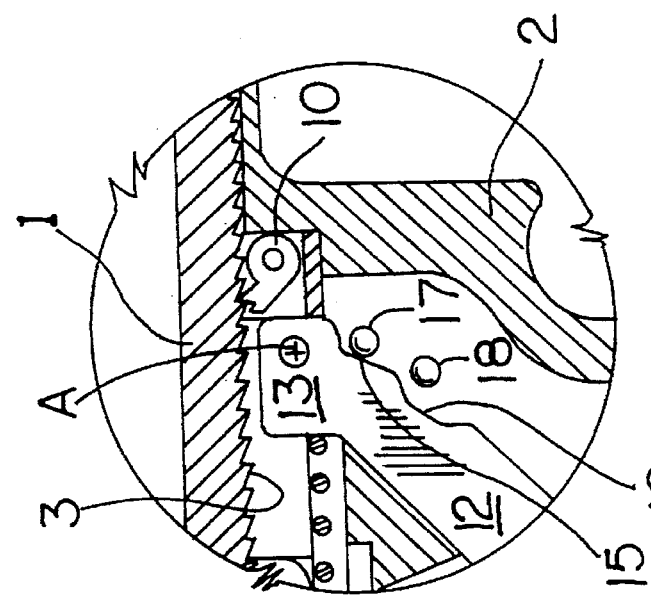

Because the first fulcrum 17 is near the output end 13, the first mechanical advantage is relatively high and a small input force yields a large output force for driving the shaft forward. This high mechanical advantage allows a large amount of pressure to be generated in the cement to force cement into bony interstices. Corresponding to the high mechanical advantage is a small movement of the shaft equal to the distance between points A and B as shown in FIG. 4. This small shaft 1 movement dispenses a relatively low volume of cement. Preferably, the trigger lever 12 rotates about the first fulcrum 17 during the first 15° of trigger travel at which point it contacts the second fulcrum 18. During this first stage of trigger travel, corresponding to rotation about the first fulcrum 17, the shaft 1 preferably travels forward 2 teeth or a distance of about 0.1". The distance the shaft moves for each degree of trigger rotation about the first fulcrum is the first advancement rate.

Figure 5:
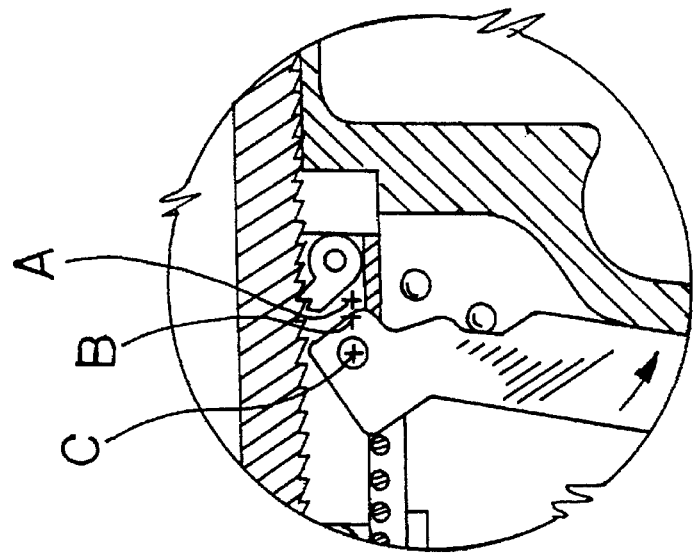
FIGS. 3–5 are side cross-sectional views of the trigger mechanism of the cement injector gun of FIG. 1 showing the operation of the trigger.

During the second stage of trigger travel, the trigger lever 12 rotates about a second center of rotation provided by the second fulcrum 18 as shown in FIG. 5. Because the second fulcrum 18 is further from the output end 13, the second mechanical advantage is relatively low. Preferably, the second mechanical advantage is from 10% to 90% of the first mechanical advantage, more preferably 25% to 50%. Corresponding to this low mechanical advantage is a relatively large shaft movement corresponding to the distance between the points B and C. This large shaft movement dispenses a large volume of cement but less pressure can be generated in the cement from a particular input force because of the lower mechanical advantage. Preferably this second stage of trigger travel corresponds to approximately 20° of trigger lever 12 rotation and moves the shaft forward 6 teeth or a distance of about 0.3". The distance the shaft moves for each degree of trigger rotation about the second fulcrum is the second advancement rate. Preferably the second advancement rate is 1.1 to 10 times the first advancement rate, more preferably 2 to 4 times.

Thus two mechanical advantages are designed into each squeeze of the trigger. The first portion of the trigger stroke produces high pressure and the second portion of the trigger stroke produces high flow volume. If high flow is desired, full strokes are used. If high pressure is desired, short strokes are used. For a typical surgical procedure, full strokes would be used to fill a bone canal. Once the canal is filled, short strokes would be used to build fluid pressure in the cement in the bone canal.

Figure 7:
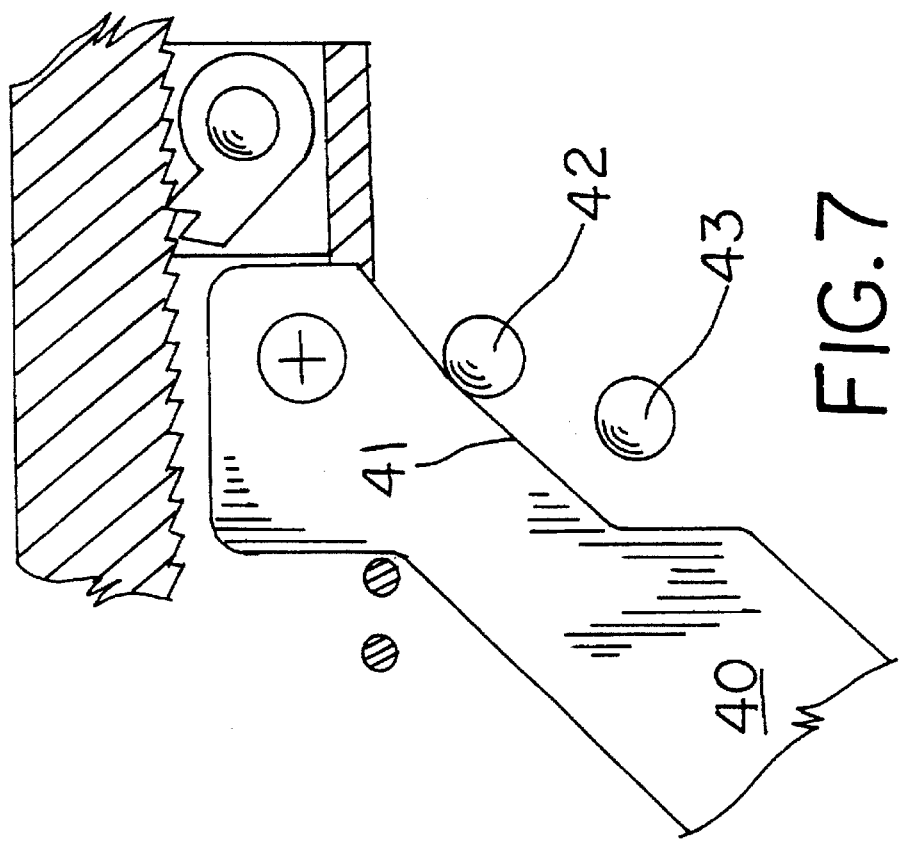
FIG. 7 is a side cross-sectional view of another alternative embodiment of the trigger mechanism of the cement injector gun of the present invention.
Figure 6:
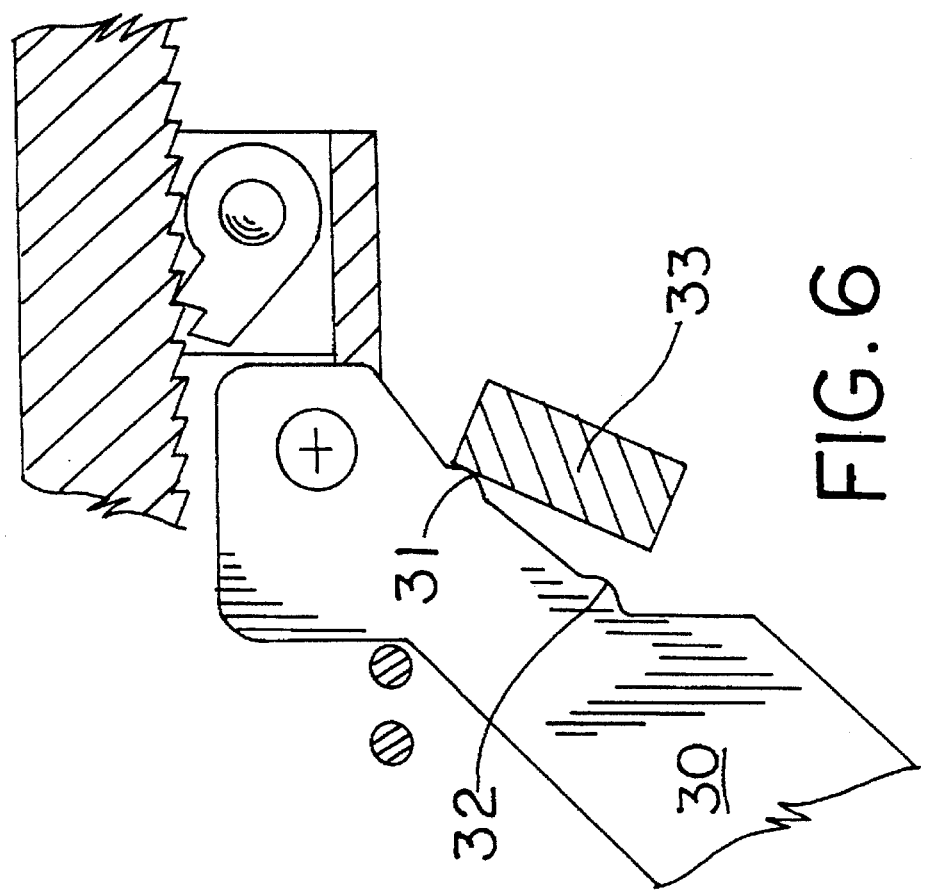
FIG. 6 is a side cross-sectional view of an alternative embodiment of the trigger mechanism of the cement injector gun of the present invention.

FIGS. 6 and 7 depict alternative embodiments of the present invention. In FIG. 6, a trigger lever 30 includes two fulcrums 31 and 32 in the form of raised areas or bumps. A bearing member 33 is attached to the housing opposite the fulcrums 31 and 32. As the trigger lever 30 is squeezed, the first fulcrum 31 initially contacts the bearing member 33 and the trigger lever 30 rotates about the first fulcrum 31 during the first stage of trigger travel. During the second stage of trigger travel, the trigger lever 30 rotates about the second fulcrum 32. In FIG. 7, a trigger lever 40 includes a flat bearing portion 41. Two fulcrums 42 and 43, similar to those depicted in FIG. 1, are attached to the housing opposite the bearing portion 41. As the trigger lever 40 is squeezed, the bearing portion 41 initially contacts the first fulcrum 42 and the trigger lever 40 rotates about the first fulcrum 42 during the first stage of trigger travel. During the second stage of trigger travel, the trigger lever 40 rotates about the second fulcrum 43. The embodiments of FIGS. 6 and 7 provide the same function as the embodiment of FIG. 1. They provide a cement injector gun having a trigger mechanism with two stages of travel provided by two fulcrums that are engaged sequentially during the trigger stroke. The first stage is characterized by a high mechanical advantage for pressurizing the bone cement and the second stage is characterized by a low mechanical advantage for extruding a large volume of bone cement. The embodiments of FIGS. 6 and 7 differ from that of FIG. 1 only in the shape and placement of the fulcrums.

Other alternatives in the construction and use of the paste injector gun can be made as well. For example, additional trigger stages each with its own mechanical advantage could be incorporated so that there would be more than two stages. By doing this, the change in mechanical advantage could be made more gradual. Also, the benefits of the paste injector gun of this invention can be used advantageously for dispensing pastes other than bone cement. Finally, it will be understood by those skilled in the art that further variations in design and construction may be made to the preferred embodiment without departing from the spirit and scope of the invention defined by the appended claims.

What is claimed is:

1. A paste injector gun comprising:
   a trigger having a range of travel with first and second stages, the first stage being from an initial rest position to an intermediate position and the second stage being from the intermediate position to a subsequent position of further trigger travel;
   first pivot means for providing a first center of rotation for the trigger, the first pivot means being engaged during the first stage of travel, the first pivot means corresponding to a first mechanical advantage; and
   second pivot means for providing a second center of rotation for the trigger, the second pivot means being engaged during the second stage of travel, the second pivot means corresponding to a second mechanical advantage, the second mechanical advantage being lower than the first mechanical advantage.

2. The paste injector gun of claim 1 further comprising a housing and wherein the first and second pivot means comprise first and second fulcrums attached to the housing and bearing portions on the trigger.

3. The paste injector gun of claim 2 wherein the fulcrums are cylindrical pins.

4. The paste injector gun of claim 1 further comprising a housing and wherein the first and second pivot means comprise first and second fulcrums attached to the trigger and a bearing member attached to the housing.

5. The paste injector gun of claim 4 wherein the fulcrums are bumps formed on the trigger.

6. The paste injector gun of claim 1 further including a cartridge adapter containing first and second parallel U-shaped slots positioned along a common axis, the first slot being sized to accept a small diameter cement cartridge and the second slot being sized to accept a large diameter cement cartridge.

7. A paste injector gun for dispensing a paste from a cartridge, the paste injector gun comprising a means for gripping the cartridge, the means for gripping the cartridge being able to grip cartridges of at least two different diameters such that the same paste injector gun can be used to dispense paste from both small and large cartridges and means for dispensing the paste from the cartridge.

8. The paste injector gun of claim 7 wherein the means for gripping the cartridge includes a cartridge adapter containing first and second parallel U-shaped slots positioned along a common axis, the first slot being sized to accept a small diameter cement cartridge and the second slot being sized to accept a large diameter cement cartridge.

9. The paste injector gun of claim 8 wherein the first slot is positioned on the common axis nearer to the means for dispensing the paste from the cartridge and the second slot is positioned on the common axis further from the means for dispensing the paste from the cartridge such that a said cartridge engaged with the first slot will extend through the second slot and a said cartridge engaged with the second slot will not extend through the first slot.

10. The paste injector gun of claim 9 wherein the first and second slots each include a peripheral groove for engaging the cartridge.

11. The paste injector gun of claim 10 wherein the first slot is at least 15% narrower than the second slot.

12. A paste injector gun comprising:
   shaft means for translation along an axis;
   advancing means for advancing the shaft along the axis, the advancing means including a trigger having a range of rotation from a rest position to a stop position, the range of rotation having first and second stages, the shaft advancing a first predetermined distance for each degree of trigger rotation in the first stage, the shaft advancing a second predetermined distance for each degree of trigger rotation in the second stage, the second predetermined distance being greater than the first predetermined distance.

13. The paste injector gun of claim 12 wherein the second predetermined distance is at least 1.1 times the first predetermined distance.

14. The paste injector gun of claim 12 wherein the second predetermined distance is from 2 to 4 times the first predetermined distance.

15. The paste injector gun of claim 12 wherein the advancing means further includes first and second fulcrums, the trigger rotating about the first fulcrum during the first stage and the trigger rotating about the second fulcrum during the second stage.

16. The paste injector gun of claim 15 wherein the trigger has an input end and an output end, the first fulcrum being closer to the output end than the second fulcrum.

17. The paste injector gun of claim 12 further including a cartridge adapter containing first and second parallel U-shaped slots positioned along a common axis, the first slot being sized to accept a small diameter cement cartridge and the second slot being sized to accept a large diameter cement cartridge.

* * * * *